US007029630B2

(12) United States Patent
Kostov

(10) Patent No.: US 7,029,630 B2
(45) Date of Patent: Apr. 18, 2006

(54) ION-SENSITIVE FLUORESCENCE OPTICAL SENSOR

(75) Inventor: Iordan V. Kostov, Baltimore, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 85 days.

(21) Appl. No.: 10/879,351

(22) Filed: Jun. 30, 2004

(65) Prior Publication Data

US 2006/0013734 A1   Jan. 19, 2006

(51) Int. Cl.
   *G01N 21/64*   (2006.01)
(52) U.S. Cl. .............................. 422/82.06; 422/82.07; 422/82.08
(58) Field of Classification Search ............. 422/82.06, 422/82.07, 82.08, 82.11
   See application file for complete search history.

(56) References Cited

U.S. PATENT DOCUMENTS 5,114,676 A    5/1992  Leiner et al.
5,691,205 A *  11/1997 Kawabata et al. .......... 436/125

OTHER PUBLICATIONS

Garoff, H. and Ansorge, W., "Improvements of DNA Sequencing Gels," *Anal. Biochem. 115:* 450-457, Academic Press, Inc. (1981).
Sheu, M.-S., et al., "Biomaterials Surface Modification Using Plasma Gas Discharge Processes," in *Encyclopedic Handbook of Biomaterials and Bioengineering, Part A. Materials*, 865-894, Wise, D.L., et al., eds., Marcel Dekker, New York (1995).
Tolosa, L., et al., "Noninvasive Measurement of Dissolved Oxygen in Shake Flasks," *Biotechnology and Bioengineering 80:*594-597, Wiley Periodicals, Inc. (2002).
Co-Pending U.S. Non-provisional Patent Application No. 10/609,720, filed Jun. 30, 2003.

* cited by examiner

*Primary Examiner*—Kiet T. Nguyen
(74) *Attorney, Agent, or Firm*—Sterne, Kessler, Goldstein & Fox PLLC

(57) ABSTRACT

The present invention relates to optical ion sensors, including fluorescence optical ion sensors for use in liquid media in the fields of biology, biotechnology, chemistry, medicine, etc. The present invention provides for optical ion sensors that may be attached to dry hydrophilic or hydrophobic surfaces so as to allow continuous sensing. The optical sensors of the present invention may be sterilized and stored for extended periods of time before use.

17 Claims, 2 Drawing Sheets

ION-SENSITIVE FLUORESCENCE OPTICAL SENSOR

STATEMENT REGARDING FEDERALLY SPONSORED RESEARCH OR DEVELOPMENT

This invention was made with U.S. government support under grant No. 0091705 awarded by the National Science Foundation. The government has certain rights to the invention.

BACKGROUND OF THE INVENTION

1. Field of the Invention

The present invention relates to optical ion sensors, including fluorescence optical ion sensors for use in liquid media in the fields of biology, biotechnology, chemistry, medicine, etc. The present invention provides for optical ion sensors that may be attached to dry hydrophilic or hydrophobic surfaces so as to allow continuous sensing. The optical sensors of the present invention may be sterilized and stored for extended periods of time before use.

2. Background of the Invention

Optical ion sensors, and specifically optical fluorescence ion sensors, rely on a chemical interaction of the ion to be analyzed with an indicator that changes its optical properties upon interaction. Generally this indicator will be a fluorescent molecule or fluorescent dye. In order to be considered a sensor (and not an assay) the indicator must be immobilized so as to keep the indicator in the field of view of the interrogation electronics, and to supply a relatively constant concentration of the indicator in the sensing area.

An indicator may be immobilized on the surface or in the bulk of a sensor. While surface immobilization ensures easy access of the ions to the indicator, the signal is usually very weak due to the extremely low thickness of the sensing layer. In addition, in complex environments, a background fluorescence often exists, which can interfere with a fluorescence measurement. A natural solution is to increase the signal intensity by immobilizing the dye in the bulk of a semi-permeable membrane, thus increasing the total amount of dye in the observation path. The membrane should be "transparent" to analyzed ions, but it should not allow the indicator molecule to leave it. The first requirement is often achieved by use of a hydrophilic (hydrogel) membrane. The second requirement is achieved by some form of entrapment (physical or chemical) of the indicator in the bulk of the polymer material.

In addition to immobilization of the indicators in a membrane material, the sensor also needs to be positioned and held by some means in front of the detection optoelectronics so as to allow for unobstructed, constant measurement of the ions in solution. Previously, this attachment has achieved by use of a mechanical holder (i.e. mesh) over the sensor. This method, however, allows solution to flow behind the sensor, thereby interfering with the optical measurement and in some cases moving the sensor out the optical pathway. U.S. Pat. No. 5,114,676 provides a pH sensor with a fluorescent indicator which may be covalently attached to a particle or to a microcrystalline cellulose fiber. The majority of the particle/indicator is imbedded within a hydrogel layer that is applied over a thermoplastic layer. The pH sensor is applied to the tip of an optical waveguide.

There exists however, a need for an optical ion sensor that can be immobilized, either permanently or semi-permanently, on dry hydrophilic or hydrophobic materials, (e.g., bioreactors, shake flasks, T-flasks, microwell plates, etc.) to allow for an unobscured light path between the interrogation optoelectronics and the sensing layer. The present application fulfills this need.

SUMMARY OF THE INVENTION

In one embodiment, the present invention provides optical ion sensors, comprising: an adhesive layer; a polymeric matrix layer, layered on the adhesive layer, comprising one or more immobilized ion-sensitive indicators; and an intermediate layer chemically bonding the adhesive layer to the polymeric matrix layer. In suitable embodiments, the optical ion sensors of the present invention may further comprise several additional layers including an optical shield layer layered to the polymeric matrix layer; a support layer having a first side layered on a side of the adhesive layer opposite of the polymeric matrix layer; a second adhesive layer having a first side layered on a second side of the support layer; and an adhesive protector layer layered on a second side of the second adhesive layer.

The support layer can be polyester foil, and in suitable embodiments, the one or more ion-sensitive indicators can comprise one or more fluorescent dyes. In certain embodiments, the polymeric matrix layer of the optical ion sensors will comprise a polymeric hydrogel and the adhesive layer will comprise silicone rubber.

In one embodiment, the present invention provides for optical ion sensors, comprising: a silicone rubber layer; a polymeric hydrogel layer, layered on the silicone adhesive layer, comprising one or more immobilized ion-sensitive fluorescent dyes; an intermediate layer chemically bonding the silicone rubber layer to the polymeric hydrogel layer; an optical shield layer layered on the polymeric hydrogel layer; a support layer having a first side layered on a side of the silicone rubber layer opposite of the polymeric matrix layer; an adhesive layer having a first side layered on a second side of the support layer; and an adhesive protector layer layered on a second side of the adhesive layer.

The present invention also provides for processes for producing an optical ion sensor, comprising: layering an intermediate layer on a first side of a silicone adhesive layer; chemically bonding a polymeric hydrogel layer comprising one or more immobilized ion-sensitive indicators to the intermediate layer; layering an optical shield layer on the polymeric hydrogel layer; layering a support layer having a first side on a side of the silicone adhesive layer opposite of the polymeric hydrogel layer; and layering an adhesive layer having a first side on a second side of the support layer.

Suitably, the layering of an intermediate layer on a first side of a silicone adhesive layer comprises plasma oxidation of the first side of the silicone adhesive layer and reaction of the first side of the silicone adhesive layer with methacrylic-reacting trimethoxysilane. Chemical bonding of the polymeric hydrogel layer to the intermediate layer suitably comprises ultraviolet illumination and bonding of the polymeric hydrogel layer to the intermediate layer.

In suitable embodiments, the processes of the present invention may further comprise layering an adhesive protector layer on a second side of the adhesive layer, and may further comprise sterilizing the optical ion sensors, e.g., via steam sterilization, radiation sterilization, or ethylene oxide sterilization.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope. The drawings are not to scale.

DETAILED DESCRIPTION OF THE INVENTION

Suitable embodiments of the present invention are now described with reference to the figures, where like reference numbers indicate identical or functionally similar elements. While specific configurations and arrangements are discussed, it should be understood that this is done for illustrative purposes only. A person skilled in the relevant art will recognize that other configurations and arrangements can be used without departing from the spirit and scope of the invention.

Figure 1:
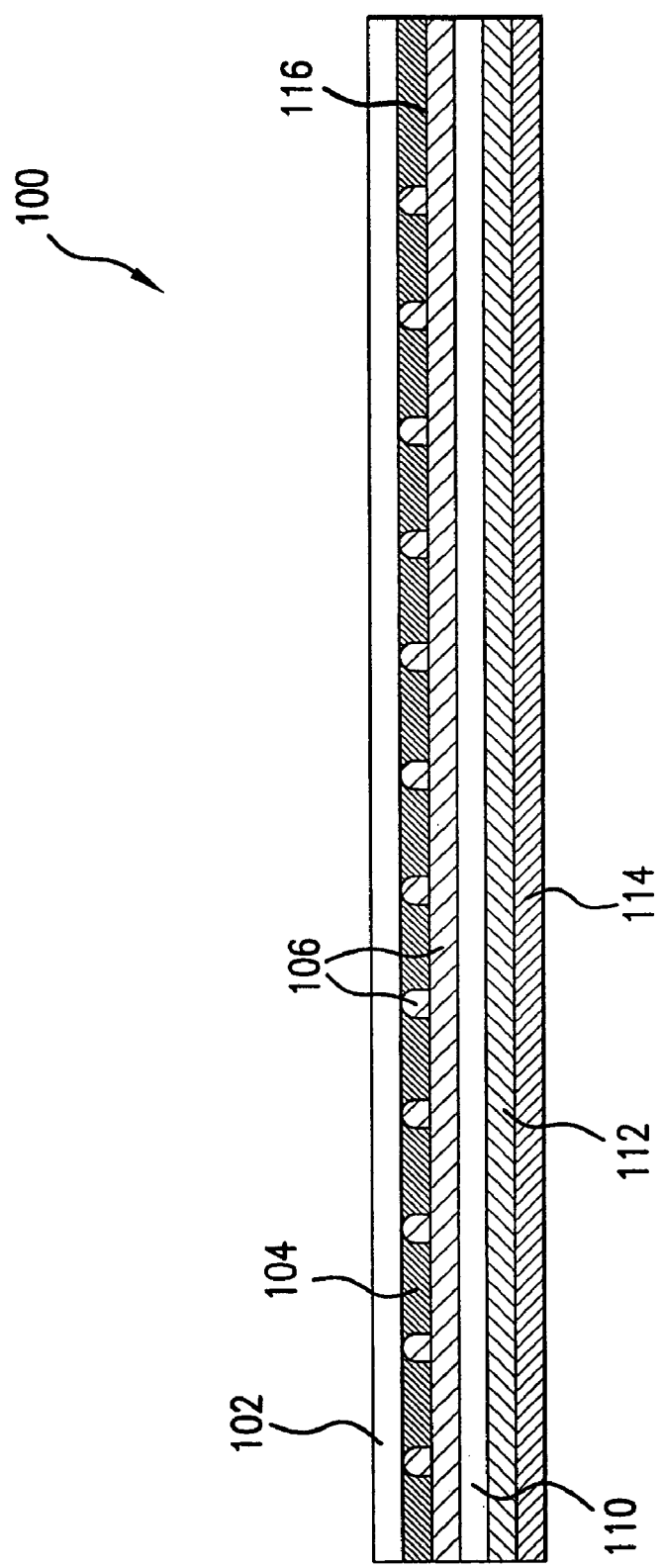
FIG. 1 shows a cross-sectional view of an optical ion sensor according to one embodiment of the present invention.

In one embodiment, the present invention provides for optical ion sensor 100 as shown in FIG. 1. Optical ion sensor 100 comprises polymeric matrix 104 which comprises one or more ion-sensitive indicators immobilized throughout the matrix. Polymeric matrix layer 104 is also referred to interchangeably herein as "sensing layer" to indicate that this layer comprises and is responsible for sensing the various ions of interest. Any ion-sensitive indicator known to the ordinarily skilled can be used in the practice of the present invention. Suitably, the one or more ion-sensitive indicators will be a fluorescent dyes. Examples of fluorescent dyes that can be used in the practice of the present invention include, but are not limited to, seminapthofluorescein, carboxynaphthofluorescein, 8-hydroxy-1,3,6-pyrene trisulphonic acid trisodium salt (HPTS), and 8-methacryloyl-6-hydroxy-1,3-pyrenedisulfonic acid (MA-HPDS). Fluorescent dyes useful in the practice of the present invention exhibit a shift in their excitation or emission wavelength, or a change in fluorescence intensity (i.e. quenching), upon interaction with a particular ion. By monitoring a change in fluorescence intensity or wavelength shift, the presence, qualitative amount, or concentration of particular ions can be determined. The present invention also embodies the use of multiple, i.e. two, three, four, five, ion-sensitive indicators in one or more polymeric matrix layers. In certain such embodiments, the optical sensors of the present invention may be used to monitor the presence, measure the qualitative or quantitative amount of several ions in solution, so long as the different indicator molecules exhibit wavelength shifts or changes in fluorescence intensity that are discernable from one another.

Any ion known to the ordinarily skilled artisan may be analyzed using the optical sensors of the present invention. For example, the optical sensors of the present invention may be used to monitor or measure ions selected from, but not limited to, oxygen (O), hydrogen (H), chlorine (Cl), sodium (Na), and potassium (K).

Polymeric matrix 104 will suitably comprise a polymeric hydrogel. Polymeric hydrogels useful in the practice of the present invention may be any hydrogel known to the ordinarily skilled artisan, and include, but are not limited to, poly(ethylene glycol) poly(2-hydroxyethyl methacrylate)-co-(methacryloyl ethyltrimethyl ammonium chloride) (pHEMA-METMA) and cross-linked polyvinyl alcohol. When the fluorescent dye MA-HPDS is utilized, it covalently binds poly(ethylene glycol) diacrylate monomer in a polymerization reaction, thus functioning as a comonomer and becomes immobilized within the poly(ethylene glycol) hydrogel. Polymeric hydrogels of the present invention can also further comprise a comonomer and/or a cross-linking agent. In suitably embodiments, the comonomer can be a siloxane-based monomer, while the cross-linking agent can be trimethylolpropane triacrylate or ethylene glycol dimethacrylate.

In certain embodiments where the fluorescent dye utilized is 8-hydroxy-1,3,6-pyrene trisulphonic acid trisodium salt (HPTS), the monomer poly(ethylene glycol) diacrylate is polymerized around the anionic exchange resin to form a hydrogel. The anionic exchange resin immobilizes the HPTS within the hydrogel via ionic binding. When the polymeric matrix comprises the copolymer poly(2-hydroxyethyl methacrylate)-co-(methacryloyl ethyltrimethyl ammonium chloride) (pHEMA-METMA) hydrogel, the fluorescent dye, suitably HPTS, ionically binds to the copolymer, thus becoming immobilized within the pHEMA-METMA hydrogel. Further description of fluorescent dye HTPS as well as polymeric hydrogels comprising pHEMA-METMA and poly(ethylene glycol) can be found in U.S. application Ser. No. 10/609,720, filed Jun. 30, 2003, and in U.S. Provisional Application Nos. 60/434,034, filed Dec. 17, 2002 and 60/478,051, filed Jun. 12, 2003.

Optical ion sensor 100 further comprises adhesive layer 106. Any suitable adhesive known to the ordinarily skilled artisan may be used in the practice of the present invention. Adhesive layer 106 must allow the passage of light to and from the optical measurement apparatus to the sensing layer, and is suitably a transparent material. Suitably, adhesive layer 106 will comprise silicone rubber. Any type of silicone known to the ordinarily skilled artisan may be used in the practice of the present invention, such as one-part, two-part, acetic acid releasing or amine releasing silicone. Adhesive layer 106 can comprise various topographical configurations, such as ridges, bumps or pillars on its surface in contact with sensing layer 104. As shown in FIG. 1, these bumps serve as spacers between adhesive layer 106 and optical shield layer 102, thereby defining the thickness of sensing layer 104, and hence the thickness of the sensing layer. Suitably, these bumps or adhesive layer 106 can be positioned in a square grid. Use of such bumps or other topographical configurations also provide for increased surface area, which results in increased mechanical strength of the chemical bonding between adhesive layer 106, intermediate layer 116, and polymeric matrix layer 104. This chemical bonding is discussed in greater detail below. The optimal thickness of sensing layer 104 can be determined by optimizing the signal from the ion-sensitive indicators, suitably a fluorescence signal, in relation to the noise, or background signal from ion-sensitive indicators immobilized throughout the sensing layer. Suitably, polymeric matrix layer 104 will be on the order of about 50 µm to about 300 µm thick, preferably about 100 µm thick. In certain embodiments, the thickness of adhesive layer 106 will suitably be between about 0.05 to about 0.5 mm, preferably about 0.1 mm thick. As used herein, when referring to any numerical value, "about" means a value of ±10% of the stated value (e.g. "about 100 µm" encompasses a range of sizes from 90 µm to 110 µm, inclusive).

Polymeric matrix layer 104 is layered on adhesive layer 106 via a chemical bonding between polymeric matrix layer 104, intermediate layer 116, and adhesive layer 106. Adhesive layer 106 is by nature a hydrophobic material, while polymeric matrix layer 104 is hydrophilic to allow the passage of water and ions through the matrix. The problem of how to attach polymeric matrix layer 104 to adhesive layer 106 has been solved by the present invention through the use of intermediate layer 116.

The term "layered" is used herein to encompass any of the terms known in the art such as formed, attached, generated, deposited, grown, bonded etc., which indicate that the various layers of the optical ion sensors of the present invention are contacted with one another in such a way, or under such conditions, that they will not become separated from each other during the normal processing, storage, shipping and use of the sensors, unless it is desired. For example, adhesive protector layer 114 may be removed from adhesive layer 112, so as to allow adhesion between adhesive layer 112 and the desired container or other sensing area.

Intermediate layer 116 may be layered on a first side of adhesive layer 106 via any method known to those skilled in the art. In suitable embodiments of the present invention, when adhesive layer 106 comprises silicone rubber layer, layering of intermediate layer 116 comprises oxidation of the silicone and creation of an intermediate monolayer between the silicone rubber and polymeric matrix layer 104.

Oxidation of the silicone adhesive layer can be performed in oxygen plasma, suitably in the range of 100–500 mTorr oxygen pressure, and 50–300 mW power. Oxidation generates a glassy, hydrophilic layer on the silicone rubber surface. Increasing the pressure and the power will increase the thickness of the hydrophilic layer. Intermediate layer 116 can be suitably prepared using a methacrylic-reacting trimethoxysilane monolayer. Intermediate layer 116 can then be bonded to polymeric matrix layer 104. (See description in Garoff and Ansorge, *Anal. Biochem.* 115:450–457 (1981) and Sheu et al. "Biomaterials Surface Modification Using Plasma Gas Discharge Processes" in Encyclopedia Handbook of Biomaterials and Bioengineering, Part A. Materials, Wise et al., eds, Marcel Dekker, NY, p. 865–894 (1995). Suitably, intermediate layer 116 will be on the order of about a few molecules thick to about 100 nanometers, preferably on the order of a few nanometers thick.

In suitable embodiments of the present invention, polymeric matrix layer 104 is chemically bound to intermediate layer 116 by placing the side of adhesive layer 106 comprising the activated intermediate layer 116 in contact with a solution of suitable polymeric monomer units that will ultimately form sensing layer 104. In certain such embodiments, this solution will comprise polyethylene glycol diacrylate monomers. Polymerization of the polymeric monomer units via any method known to the ordinarily skilled artisan generates sensing layer 104 to which intermediate layer 116 is chemically bonded, and hence polymeric matrix layer 104 and adhesive layer 106 are thereby chemically bonded. Suitable methods of polymerization include, but are not limited to, illumination with ultraviolet (UV) light, introduction of a catalyst or initiator, heat induction and other known methods of generating free radicals.

Optical ion sensors produced in accordance with the present invention that comprise sensing layer 104 comprising one or more immobilized ion-sensitive indicators, intermediate layer 116 and adhesive layer 106 can be used to measure the presence and/or concentration of one or more ions in a solution as described herein by attaching the optical ion sensors to an appropriate vessel or container that contains the solution of interest. The optical sensors of the present invention can also comprise additional functional layers as described throughout that can enhance or extend their use as optical ion sensors.

In suitable embodiments of the present invention, optical ion sensor 100 will further comprise optical shield 102 layered on polymeric matrix layer 104 on a side opposite adhesive layer 106. Optical shield 102 is permeable to ions, but stops light from entering a sample solution, thereby reducing background noise from the sample. In certain such embodiments when one or more fluorescent dyes are utilized as the immobilized ion-sensing indicators, optical shield 102 prevents fluorescent excitation light from the measuring optics and emission light from the fluorescent dye from entering the sample solution. Optical shield 102 also prevents ambient light from entering the sensing layer and interfering with the measurement of the fluorescent signal from the fluorescent dyes. Optical shield 102 may be about 5 µm to about 100 µm thick, and suitably comprises a sheet of filter paper or a polysulfone microfiltration membrane, but any material layer that will allow passage of ions while preventing the passage of light can be used in the practice of the present invention.

In order to provide additional mechanical strength to the optical sensors of the present invention, as shown in FIG. 1, support layer 110, having a first side, can suitably be layered on the side of adhesive layer 106 opposite of the polymeric matrix layer 104. Support layer 110 can comprise any material that will allow the passage of light to and from the optical measurement apparatus and the sensing layer 104, and also provide increased stiffness and mechanical strength. Suitably, support layer 110 is a transparent, thin (about 0.05 mm to 0.5 mm in thickness, preferably about 0.1 mm thick) polymeric material to which adhesive layer 106 can be attached, including polyester and polyethylene polymer films. Use of support layer 110 allows for a thinner polymeric matrix layer, and therefore a thinner overall optical sensor.

Optical ion sensor 100 may further comprise a second adhesive layer 112, having a first side, layered on a second side of support layer 110, opposite the first adhesive layer 106. When used in conjunction with support layer 110, this second adhesive layer allows the optical ion sensor to be attached to the surface of a container or vessel comprising a sample solution of interest. The nature of this second adhesive layer will dictate the strength, and therefore duration, of attachment to the container or vessel. Suitably, second adhesive layer 112 can be a second layer of silicone rubber, or can be a layer of any adhesive known to the ordinarily skilled artisan that will allow adhesion between the surface of a container or vessel and the optical ion sensor, such as double sided tape. Second adhesive layer 112 must allow the passage of light to and from the optical measurement apparatus to the sensing layer, and is suitably a transparent material. Suitably, second adhesive layer 112 is about 0.05 to about 0.5 mm, preferably about 0.1 mm thick. This second adhesive layer can further comprise an adhesive protector layer 114 layered on a second side of the second adhesive layer so as to keep the second adhesive layer from attaching to surfaces prior to attachment to the container or vessel of interest, and also to protect the adhesive layer from drying or from contact with dust, dirt, and other particulates. In suitable embodiments, this adhesive protector layer can be any material that will protect the adhesive layer from drying and attachment to other surfaces or particulates, but can be easily removed when it is desired that the optical ion sensor be attached to the surface of a container or vessel of interest. Suitable materials include thin (about 10 µm to about 0.5 mm) layers of polymers, plastics and glass, though thicker layers of glass or plastics, on the order of a several millimeters, may be used as adhesive protector layer 114.

Optical ion sensors of the present invention are generally square or rectangular in shape (though other shapes are encompassed within the embodiments of the present invention) and suitably in the range of about 1–3 $cm^2$ in surface area and about 0.5 mm to about 1 mm in thickness.

The present invention also provides for processes for producing the optical ion sensors discussed throughout. Such processes comprise layering an intermediate layer on a first side of a first adhesive layer. This adhesive layer can be any suitable adhesive, including silicone rubber. Any process known to the ordinarily skilled artisan that can be used to create a reactive surface on the adhesive layer can be used in the practice of the present invention. Suitably, when silicon rubber is used as the adhesive layer, the layering of an intermediate layer will comprise plasma oxidation of a first side of the silicone adhesive layer and reaction of the first side of the silicon adhesive layer with methacrylic-reacting trimethoxysilane.

A polymeric matrix layer, suitably a polymeric hydrogel, comprising one or more immobilized ion-sensitive indicators (e.g. fluorescent dyes), can then be chemically bound to the intermediate layer on the adhesive layer. This chemical bonding can take place via any mechanism or chemical reaction known to the ordinarily skilled artisan, and suitably, will comprise ultraviolet illumination of the polymeric matrix layer to bond the polymer to the intermediate layer on the surface of the adhesive layer.

An optical shield layer, suitably a layer of filter paper or other membrane, can then be layered on the polymeric matrix layer so as to provide a membrane that allows passage of ions into the sensing layer, but does not allow fluorescent light to enter the sample solution. The processes of the present invention also provide for a support layer, having a first side, to be layered on a side of the first adhesive layer opposite of the polymeric matrix layer. This support layer can comprise any material that provides additional support and mechanical strength to the optical sensor, while still allowing for the passage of light and from to the interrogatory optics. The processes of the present invention also comprise layering a second adhesive layer, suitably silicone rubber or other adhesive having a first side, on a second side of the support layer. This second adhesive layer will allow the optical ion sensors produced by the processes of the present invention to be attached, either permanently or semi-permanently, to the surface of a container or vessel of interest.

In further embodiments, the processes of the present invention provide for the layering of an adhesive protector layer to a second side of the second adhesive layer. This adhesive protector layer can comprise any suitable material (e.g. thin layer of polymers or plastics) that will protect the second adhesive layer from contact with other surfaces or unwanted particulates.

The processes of the present invention can further comprise sterilizing any of the optical ion sensors embodied by the present invention. Sterilization allows for the optical ion sensors to be placed in environments where the presence of bacteria or other contaminants could be harmful or detrimental to the solution being analyzed. For example, use of the optical ion sensors of the present invention in applications such as bioreactors would require the sensors to be free of bacteria so as not to contaminate the reaction taking place in the solution of interest.

Any sterilization method known to the ordinarily skilled artisan can be used to sterilize the optical ion sensors of the present invention. Suitable sterilization methods include, but are not limited to, steam sterilization, radiation sterilization and ethylene oxide sterilization. The various layers of the optical ion sensors of the present invention are layered or bound such that such sterilization methods will not weaken these junctions.

In another embodiment, the present invention provides for methods of measuring the presence and/or concentration of one or more ions in a liquid solution using the optical ion sensors of the present invention. The optical ion sensors of the present invention are attached to a surface of a transparent container or vessel comprising a solution of interest. The sensors of the present invention can be attached to both hydrophilic and hydrophobic surfaces (e.g., plastics, polymers, glasses), such as the inside of bioreactors, shake flasks, T-flasks, microwell plates, etc. The optical sensors of the present invention can be attached to the sides of the desired container, or to the bottom, provided that the sensors are in the field of view of the interrogating optoelectronics. The optical ion sensors of the present invention can be used in any method or apparatus which requires the analysis of the presence and/or concentration of ions in solution, including in fields such as biology, biotechnology, medicine, chemistry, etc.

As described herein, the invention provides a number of advantages and uses. The embodiments and variations described in detail herein are to be interpreted by the appended claims and equivalents thereof. The following examples are given for the purpose of illustrating various embodiments of the invention and are not meant to limit the present invention in any fashion.

EXAMPLE 1

Preparation of an Ion-Sensitive Fluorescence Optical Sensor

Preparation of the optical ion sensors of the invention suitably begins with the adhesive layer. As such, a layer of silicone rubber is used. By its hydrophobic nature, silicone rubber sticks well to many surfaces. Any type of silicone can be used (one part, two-part, acetic acid releasing, amine releasing, etc.) A sheet of silicone rubber is prepared (RTV117 (General electric)) with approximate thickness of 0.5 mm by spreading it with spatula on the flat surface of a polypropylene block. As the adhesion to the polypropylene is not significant, the sheet can be easily removed after 24 h of curing at room temperature.

In order to provide greater stiffness of the adhesive layer, it can be reinforced with support layer (i.e. polyester). In this case, the uncured silicone rubber is spread on polyester foil (0.1 mm thick) at a thickness of 0.1–0.2 mm. When it cures, on the back side of the polyester foil, a second layer of silicone rubber can be added, or alternatively a layer of another adhesive (i.e. a double sided pressure-sensitive adhesive, like double sided Scotch™ tape). The nature of this second layer determines the strength of attachment to the transparent container.

The silicone rubber layer can be shaped in ridges, bumps, pillars, etc. to serve as spacers that determine the thickness of sensing layer. Here, the silicone layer is prepared with bumps positioned in a square grid.

The silicone layer is then prepared to be chemically bonded to the sensing polymeric matrix layer. The activation consist of two steps: a) oxidation of the silicone and b) creation of an intermediate monolayer between the silicone rubber and the future polymeric hydrogel layer.

Oxidation is performed in oxygen plasma, at 100–500 mTorr oxygen pressure, and 50–300 mW power. After this step a glassy, hydrophilic layer is formed on the silicone rubber surface. The higher the pressure and the power, the thicker the layer that will be formed. Right after the oxidation the silicone-polyester foil is placed in DI water so it is completely covered with water for several minutes (5 to 10 min). An indication that the oxidation went well is the hydrophilicity of the silicone rubber surface (i.e., it is wet when taken out of the water). The foil is then placed in vacuum oven (70° C., 1 Torr) and completely dried.

The intermediate layer is prepared with methacrylic-reacting trimethoxysilane monolayer. 1 ml glacial acetic acid is dissolved in 10 ml deionized water, and 200 μl [3-(Methacryloyloxy)propyl] trimethoxysilane (M6514, Aldrich) are dissolved in 20 ml absolute ethanol. 600 μl of the first glacial acetic acid solution are added to the ethanol solution just prior to use. The surface of the oxidized and dried silicon rubber is treated with this mixture for 5 minutes, then washed 3 times with absolute ethanol and dried.

The silicone (or silicone/polyester) foil is then ready to be bonded to the sensing polymeric hydrogel layer. Choice of hydrogel depends on the ion type that is to be detected. The present example utilizes a pH sensing hydrogel, but other hydrogels can be substituted to detect other ions.

250 mg PEG (polyethylene glycol diacrylate, 4000 MW), 1.2 ml 7.2 PBS (phosphate buffer saline), and 0.6 ml 10 mg/ml solution of acrylate derivative of DHDS dihydroxy-disulfonic acid) are thoroughly mixed together using a Vortex homogenizer. 36 ml photoinitiator (Darocur, Ciba) are added. The solution is then mixed thoroughly again and spread on the material that will be used for the optical shield (Whatman filter paper No. 1 or a polysulfone microfiltration membrane are used here). The solution must "wet" the backing entirely; this ensures that the backing will be held in place with sufficient mechanical strength. The wet backing is then placed on a piece of glass. The silicone layer is positioned on top of the hydrogel solution with the activated side of the silicon layer (i.e. the intermediate layer) toward the backing. A second piece of glass is then placed over the silicon layer and then the entire stack is clamped together. The stack is then illuminated for 4 to 15 min from the both sides at 10 cm distance with 200 W UV longwave lamp. The thicker the sensing layer, the longer the illumination time required. After polymerization, the resulting patch structure is washed extensively with deionized water in order to remove any unbound dye.

Figure 2:
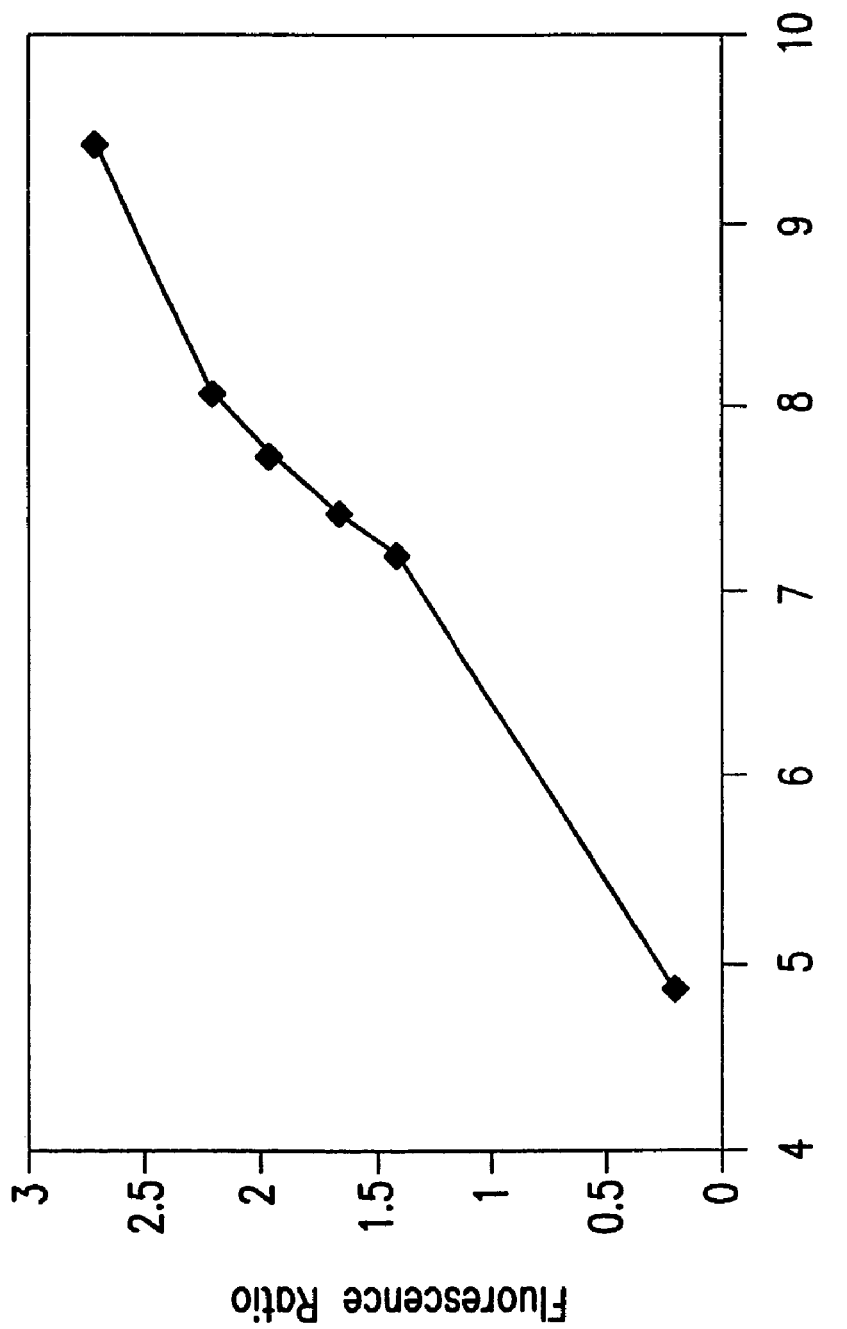
FIG. 2 shows a calibration curve of Fluorescence ratio versus pH.

Calibration of a pH-sensitive optical sensor according to one embodiment of the present invention is represented in FIG. 2 as fluorescence ratio vs. pH.

Any patents, patent applications or publications mentioned in this specification are indicative of the levels of those skilled in the art to which the invention pertains. Further, these patents, patent applicants and publications are incorporated by reference herein to the same extent as if each individual publication was specifically and individually incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention.

Changes therein and other uses will occur to those skilled in the art which are encompassed within the spirit of the invention as defined by the scope of the claims.

What is claimed is:

1. An optical ion sensor, comprising:
   (a) an adhesive layer;
   (b) a polymeric matrix layer, layered on said adhesive layer, comprising one or more immobilized ion-sensitive indicators; and
   (c) an intermediate layer chemically bonding said adhesive layer to said polymeric matrix layer.

2. The optical ion sensor of claim 1, further comprising an optical shield layer layered on said polymeric matrix layer.

3. The optical ion sensor of claim 1, further comprising a support layer having a first side layered on a side of said adhesive layer opposite of said polymeric matrix layer.

4. The optical sensor of claim 3, wherein said support layer comprises polyester foil.

5. The optical ion sensor of claim 3, further comprising a second adhesive layer having a first side layered on a second side of said support layer.

6. The optical ion sensor of claim 5, further comprising an adhesive protector layer layered on a second side of said second adhesive layer.

7. The optical ion sensor of claim 1, wherein said one or more ion-sensitive indicators comprise one or more fluorescent dyes.

8. The optical ion sensor of claim 1, wherein said polymeric matrix layer comprises a polymeric hydrogel.

9. The optical ion sensor of claim 1, wherein said adhesive layer comprises silicone rubber.

10. An optical ion sensor, comprising:
    (a) a silicone rubber layer;
    (b) a polymeric hydrogel layer, layered on said silicone adhesive layer, comprising one or more immobilized ion-sensitive fluorescent dyes;
    (c) an intermediate layer chemically bonding said silicone rubber layer to said polymeric hydrogel layer;
    (d) an optical shield layer layered on said polymeric hydrogel layer;
    (e) a support layer having a first side layered on a side of said silicone rubber layer opposite of said polymeric matrix layer;
    (f) an adhesive layer having a first side layered on a second side of said support layer; and
    (g) an adhesive protector layer layered on a second side of said adhesive layer.

11. The optical ion sensor of claim 10, wherein said support layer comprises polyester foil.

12. A process for producing an optical ion sensor, comprising:
    (a) layering an intermediate layer on a first side of a silicone adhesive layer;
    (b) chemically bonding a polymeric hydrogel layer comprising one or more immobilized ion-sensitive indicators to the intermediate layer;
    (c) layering an optical shield layer on the polymeric hydrogel layer;
    (d) layering a support layer having a first side on a side of the silicone adhesive layer opposite of the polymeric hydrogel layer; and (e) layering an adhesive layer having a first side on a second side of the support layer.

13. The process of claim 12, wherein said layering of an intermediate layer in (a) comprises plasma oxidation of the first side of the silicone adhesive layer and reaction of the first side of the silicone adhesive layer with methacrylic-reacting trimethoxysilane.

14. The process of claim 12, wherein said chemical bonding in (b) comprises ultraviolet illumination and bonding of the polymeric hydrogel layer to the intermediate layer.

15. The process of claim 12, further comprising (f) layering an adhesive protector layer on a second side of the adhesive layer.

16. The process of claim 12, further comprising sterilizing the optical ion sensor.

17. The process of claim 16, wherein said sterilization comprises steam sterilization, radiation sterilization, or ethylene oxide sterilization.

* * * * *

UNITED STATES PATENT AND TRADEMARK OFFICE
Certificate

Patent No. 7,029,630 B2                                                                              Patented: April 18, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Iordan V. Kostov, Baltimore, MD (US); and Govind Rao, Columbia, MD (US).

Signed and Sealed this Twenty-ninth Day of May 2007.

ROBERT KIM
*Supervisory Patent Examiner*
Art Unit 2881